(12) United States Patent
Wynberg et al.

(10) Patent No.: US 6,441,207 B1
(45) Date of Patent: Aug. 27, 2002

(54) METHOD FOR MAKING HYDROXY-25-ENE-VITAMIN D COMPOUNDS

(75) Inventors: Hans Wynberg; Ton Vries; Kees Pouwer, all of Groningen (NL)

(73) Assignee: Bone Care International, Inc., Middleton, WI (US)

( * ) Notice: Subject to any disclaimer, the term of this patent is extended or adjusted under 35 U.S.C. 154(b) by 0 days.

(21) Appl. No.: 09/716,316

(22) Filed: Nov. 20, 2000

Related U.S. Application Data

(63) Continuation of application No. PCT/US99/11950, filed on May 28, 1999.
(60) Provisional application No. 60/087,222, filed on May 29, 1998.

(51) Int. Cl.[7] .................... C07C 401/00; C07C 403/00
(52) U.S. Cl. .............................. 552/653; 552/653
(58) Field of Search ................... 552/653; 514/167

(56) References Cited

U.S. PATENT DOCUMENTS

| | | |
|---|---|---|
| 4,225,596 A | 9/1980 | DeLuca |
| 4,310,511 A | 1/1982 | Holick |
| 4,388,243 A | 6/1983 | Nishikawa et al. |
| 4,391,802 A | 7/1983 | Suda et al. |
| 4,749,710 A | 6/1988 | Truitt et al. |
| 5,030,772 A | 7/1991 | DeLuca et al. |
| 5,035,783 A | 7/1991 | Goethals et al. |
| 5,252,191 A | 10/1993 | Pauli et al. |
| 5,518,725 A | 5/1996 | Daynes et al. |
| 5,540,919 A | 7/1996 | Daynes et al. |
| 5,559,104 A | 9/1996 | Romeo et al. |
| 5,562,910 A | 10/1996 | Daynes et al. |
| 5,589,471 A | 12/1996 | Hansen et al. |
| 5,710,294 A | 1/1998 | DeLuca et al. |
| 5,716,946 A | 2/1998 | DeLuca et al. |
| 5,880,114 A | 3/1999 | DeLuca et al. |

FOREIGN PATENT DOCUMENTS

WO    WO 92 12165 A    7/1992

OTHER PUBLICATIONS

Christiansen, C., et al., 11 Eur. J. Clin. Invest., 305–309 (1981).
Holick, M. F., et al., 68 Proc. Natl. Acad. Sci. USA, 803–804 (1971).
Jones, G., et al., 14 Biochemistry, 1250–1256 (1975).
Holick, M. F., et al., 180 Science 190–191 (1973).
Lam, H. Y., et al., 186 Science, 1038–1040 (1974).
Ott, S. M. and C. H. Chesnut, 110 Ann. Int. Med., 267–274 (1989).
Gallagher, J. C., et al., 113 Ann. Int. Med., 649–655 (1990).
Aloia, J., et al., 84 Amer. J. Med., 401–408 (1988).
Shiraki, M., et al., 32 Endocrinol. Japan, 305–315 (1985).
Jensen, G. F., et al., 16 Clin. Endocrinol., 515–524 (1982).
Sorensen et al., 7 Clin. Endocrinol., 169S–175S (1977).
Orimo et al., 3 Bone and Mineral., 47–52 (1987).
Miller et al., 52 Cancer Res., 515–520 (1992).
Skowronski et al., 136 Endocrinology, 20–26 (1995).
White et al., 1 J. Chem. Soc. Perkin Trans., 759 (1993).
Nishigaichi et al., Chem. Lett., 961 (1996).
Manchand et al., 60 J. Org. Chem., 6574 (1995).
Calverley, Tetrahedron 51, 1609 (1987).
Walba et al., J. Org. Chem. 53, 1046 (1998).
Smith III et al., J. Am. Chem. Soc. 103, 1996 (1981).

*Primary Examiner*—Sabiha Qazi
(74) *Attorney, Agent, or Firm*—Michael Best & Friedrich LLP; Teresa J. Welch; Jill A. Fahrlander

(57) ABSTRACT

The present invention provides a method for preparing a novel class of vitamin D compounds in which the C-25 or equivalent position has a double bond. In addition, the side chain is optionally extended by one or two methylene or methyne groups. The compounds prepared by the method of the present invention are of value as prodrugs for active 1α, 24-dihydroxylated vitamin D compounds.

7 Claims, 4 Drawing Sheets

METHOD FOR MAKING HYDROXY-25-ENE-VITAMIN D COMPOUNDS

CROSS-REFERENCE TO RELATED APPLICATIONS

This application is a continuation of PCT/US99/11950 filed May 28, 1999 and U.S. Provisional Application No. 60/087,222 filed May 29, 1998.

BACKGROUND OF THE INVENTION

This invention related generally to vitamin D compounds and in particular, to vitamin D compounds in which the C-25 or equivalent position is double bonded, and specifically to a method of making such compounds.

Vitamin D has long been established as having an important biological role in bone and mineral metabolism. For example, vitamin D plays a critical role in stimulating calcium absorption and regulating calcium metabolism. It is also known that it is not vitamin D itself, but metabolites generated from it in vivo that are effective in regulating calcium metabolism. The discovery of active forms of vitamin D, (M. F. Holick et al., 68 *Proc. Natl. Acad. Sci. USA*, 803–804 (1971); G. Jones et al., 14 *Biochemistry*, 1250–1256 (1975), and other active vitamin D analogs (M. F. Holick et al., 180 Science 190–191 (1973); H. Y. Lam et al., 186 *Science* 1038–1040 (1974) caused much excitement and speculation about the usefulness of these vitamin D compounds in the treatment of bone depletive disorders.

Animal studies examining the effects of these active vitamin D compounds, particularly 1α,25-dihydroxyvitamin $D_3$, the hormonally active form of vitamin $D_3$, suggested that such agents would be useful in restoring calcium balance. An early clinical study indicated that oral administration of 0.5 μg/day of 1α,25-dihydroxyvitamin $D_3$ to a group of postmenopausal women improved intestinal calcium absorption as well as calcium balance in the women. On this basis, U.S. Pat. No. 4,225,596 ("'596 Patent") described and claimed the use of 1α,25-dihydroxyvitamin $D_3$ for increasing calcium absorption and retention, i.e., this compound is highly potent in stimulating intestinal calcium absorption as well as the resorption of calcium from bone (i.e., bone mobilization).

The best indicator of the efficacy of vitamin D compounds, however, in the prevention or treatment of depletive bone disorders, however, is bone itself rather than calcium absorption or calcium balance. More recent clinical data indicate that, at the dosage ranges taught in the '596 Patent, 1α,25-dihydroxy-vitamin $D_3$ has, at best, modest efficacy in preventing or restoring loss of bone mass or bone mineral content (S. M. Ott and C. H. Chesnut, 110 *Ann. Int. Med.* 267–274 (1989); J. C. Gallagher et al., 113 *Ann. Int. Med.* 649–655 (1990); J. Aloia et al., 84 *Amer. J. Med.* 401–408 (1988)).

These clinical studies with 1α,25-dihydroxyvitamin $D_3$, and another conducted with 1α-hydroxyvitamin $D_3$ (M. Shiraki et al., 32 *Endocrinol. Japan* 305–315 (1985)), indicate that the capacity of these two vitamin D compounds to restore lost bone mass or bone mineral content is dose-related. The studies also indicate, however, that, at the dosage ranges required for either compound to be truly effective, toxicity in the form of hyperclacemia and hypercalciuria becomes a major problem. Specifically, attempts to increase the amount of 1α,25-dihydroxyvitamin $D_3$ above 0.5 μg/day have frequently resulted in toxicity. At dosage levels below 0.5 μg/day, no effects are observed on bone mass or mineral content. (See, G. F. Jensen et al., 16 *Clin. Invest.* 305–309 (1981)). Two μg/day of 1α-hydroxyvitamin $D_3$ was found to have efficacy in increasing bone mass in patients exhibiting senile osteoporosis (O. H. Sorensen et al., 7 *Clin. Endocrinol.* 169S–175S (1977)). Data from clinical studies in Japan, a population that has low calcium intake, indicate that efficacy is found with 1α-hydroxyvitamin $D_3$ when administered at 1 μg/day (M. Shiraki et al., 32 *Endocrinol. Japan.* 305–315 (1985); H. Orimo et al., 3 *Bone and Mineral* 47–52 (1987)). At 2 μg/day, however, toxicity with 1α-hydroxyvitamin $D_3$ occurs in approximately 67 percent of the patients, and at 1 μg/day, this percentage is approximately 20 percent. Thus, the 1α-hydroxylated vitamin $D_3$ compounds can produce dangerously elevated blood calcium levels due to their inherent calcemic activity.

Because of their toxicity, 1-hydroxylated vitamin $D_3$ compounds can only be administered in oral dosages that are, at best, modestly beneficial in preventing or treating loss of bone or bone mineral content. Indeed, Aloia recommends that alternative routes of administration be sought which might avoid the toxicity problems and allow higher dosage levels to be achieved. (J. Aloia et al., 84 *Amer. J. Med.* 401–408 (1988)). Despite reported toxicities of 1α-hydroxyvitamin $D_3$ and 1α,25-dihydroxyvitamin $D_3$, these two compounds remain the drugs of choice for many bone depletive disease treatments and calcium metabolism disorders such as renal osteodystrophy, hypoparathyroidism, vitamin D-resistant rickets and osteoporosis.

These two drugs also remain the only approved forms of 1α-hydroxylated vitamin D for treating or preventing hyperparathyroidism which occurs secondary to the renal disease, although both drugs are not currently approved in all major pharmaceutical markets.

More recently, in addition to vitamin D's role in regulating calcium homeostatis, other biological roles for vitamin D have come to light. Specific nuclear receptors for 1α,25-dihydroxyvitamin $D_3$ have been found in cells from diverse organs not involved in calcium homeostasis. For example, Miller et al., 52 *Cancer Res.* (1992) 515–520, have demonstrated biologically active, specific receptors for 1,α25-dihydroxyvitamin $D_3$ in the human prostatic carcinoma cell line, LNCaP.

It has been also shown that certain vitamin D compounds and analogs are potent inhibitors of malignant cell proliferation and inducers/stimulators of cell differentiation. For example, U.S. Pat. No. 4,391,802 issued to Suda et al. discloses that 1α-hydroxyvitamin D compounds, specifically 1α,25-dihydroxyvitamin $D_3$ and 1α-hydroxyvitamin $D_3$, possess potent antileukemic activity by virtue of inducing the differentiation of malignant cells (specifically leukemia cells) to nonmalignant macrophages (monocytes), and are useful in the treatment of leukemia. Additionally, Skowronski et al., 136 *Endocrinology* 20–26 (1995), have reported antiproliferative and differentiating actions of 1α,25-dihydroxyvitamin $D_3$ and other vitamin $D_3$ analogs on prostate cancer cell lines.

Still other roles for vitamin D have been suggested in the modulation of the immune response (see, e.g., U.S. Pat. No. 4,749,710 issued to Truitt et al.; U.S. Pat. No. 5,559,107 issues to Gates et al., U.S. Pat. Nos. 5,540,919, 5,518,725 and 5,562,910 issued to Daynes et al.; U.S. Pat. No. 5,880,114 issued to DeLuca et al.) and the inflammatory response (see, e.g., U.S. Pat. No. 5,589,471 issued to Hansen et al.) as well as treatment of multiple sclerosis (see, U.S. Pat. No. 5,716,946 issued to DeLuca et al.).

Nonetheless, despite their activity in diverse biological functions the fact remains that at the levels required in vivo for effective use, e.g., as antileukemic agents, the known vitamin D compounds can induce markedly elevated and potentially dangerous blood calcium levels by virtue of their inherent calcemic activity. That is, the clinical use of active vitamin D compounds such as 1α,25-dihydroxyvitamin $D_3$ and other vitamin $D_3$ analogs is precluded, or severely limited, because of their equally high potency as agents affecting calcium metabolism, i.e., by the risk of hypercalcemia. Considering the diverse biological actions of vitamin D and its potential as a therapeutic agent, a need exists for compounds with greater specific activity and selectivity of action, e.g., vitamin D compounds with antiproliferative and differentiating effects but which have less calcemic activity than therapeutic amounts of the known compounds or analogs of vitamin D.

BRIEF SUMMARY OF THE INVENTION

The present invention provides a method for preparing hydroxy-25-ene-vitamin D compounds. These compounds are considered of value as pharmaceuticals because of their vitamin D activity but low toxicity when compared to the known vitamin D compounds. Specifically, these compounds are hydroxy-25-ene-vitamin D, such as 1α-hydroxy-25-ene-vitamin D compounds and 24-hydroxy-25-ene-vitamin D compounds. These compounds are suitably prodrugs for 1α,24-dihydroxylated vitamin D compounds as they are hydroxylated in vivo at the 24-position in the case of the 1α-hydroxy-25-ene-vitamin D compounds and in the 1α-position in the case of the 1α-hydroxy-25-ene-vitamin D compounds to become the active forms of vitamin D. As prodrugs, these compounds in effect circumvent the first pass concern over intestinal vitamin D receptor binding which mediates intestinal calcium absorption, thereby resulting in reduced or no hypercalcemia compared with similar dosing with known active vitamin D compounds such as 1α,25-dihydroxyvitamin $D_3$.

The foregoing, and other advantages of the present invention, are realized in one aspect thereof in a method of making hydroxy-25-ene-vitamin D compounds. The 25-ene-vitamin D compounds are either 1α-hydroxylated or 24-hydroxylated so that when administered to a human or an animal, they become dihydroxylated to active 1α,24-dihydroxylated vitamin D compounds. The method includes reacting the appropriate vitamin D starting material with $SO_2$ and protecting the hydroxyl functionality at C-3 and/or C-1 with t-butyldimethylsilyloxychloride to afford an $SO_2$ adduct. Ozonolysis and reduction of the $SO_2$ adduct severs the C-17 side chain and affords a truncated side chain C-22 alcohol. $SO_2$ extrusion, and subsequent oxidation using the known Swern oxidation affords a C-22 aldehyde. The side chain is reassembled by reaction of the C-22 aldehyde with an appropriate phenyl sulfone to yield a 1α-hydroxy-25-ene-vitamin D compound or a 25-ene-vitamin D compound depending upon the nature of the starting material.

If the 24-hydroxylated 25-ene-vitamin D compound is the desired end product, the 25-ene-vitamin D compound is incubated with human hepatoma cells, and the 24-hydroxy metabolite is isolated and purified to yield the 24(S)-25-ene-vitamin D compound.

Specifically, the invention provides a method of making hydroxy-25-ene-vitamin D compounds comprising the steps of reacting a 2,3-dimethyl-3-butene phenyl sulfone with a hydroxyl-protected C-22 aldehyde of a vitamin D, the vitamin D being hydroxyl-protected at C-3 or at C-3 and C-1.

The 2,3-dimethyl-3-butene phenyl sulfone is prepared by methylating, isomerizing and hydrolyzing ethyl dimethylacrylate to yield a dimethyl-3-ene-butanoic acid; amidating the dimethyl-3-ene-butanoic acid with oxazolidone to form oxazolidinones; separating the oxazolidinones to the desired isomer; oxidizing and reducing the desired isomer to yield a methyl-3-ene-butanol; reacting with methane sulfonyl chloride to form a mesylate; and substituting a phenyl sulfone group for the mesylate group to yield the 2,3-dimethyl-3-butene phenyl sulfone.

The hydroxyl-protected C-22 aldehyde of vitamin D is prepared by hydroxyl-protecting the C-3 position of vitamin $D_2$ to yield a C-3 hydroxyl-protected vitamin $D_2$; sulfonating the C-3 hydroxyl-protected vitamin $D_2$ to yield a $SO_2$ adduct; subjecting the adduct to $SO_2$ extrusion to yield the trans-C-3-hydroxyl-protected vitamin $D_2$; hydroxylating the trans-C-3-hydroxyl-protected vitamin $D_2$ at the C-1 position; hydroxyl protecting the C-1 position; forming a $SO_2$ adduct; truncating the C-17 sidechain to form a C-22 alcohol; and subjecting the C-22 alcohol to $SO_2$ extrusion and Swern oxidation to form the C-22 aldehyde. The method of the present invention further includes reducing, isomerizing, deprotecting and irradiating the hydroyxl-protected-25-ene-vitamin D produced from the reaction of the phenyl sulfone and the C-22 aldehyde to yield a hydroxy-25-ene-vitamin $D_2$.

If 25-ene-vitamin $D_2$ compounds are desired, the hydroxyl-protected C-22 aldehyde of vitamin D is prepared by hydroxyl-protecting the C-3 position of vitamin $D_2$ to yield a C-3 hydroxyl-protected vitamin $D_2$; sulfonating the C-3 hydroxyl-protected vitamin $D_2$ to yield a $SO_2$ adduct; truncating the C-17 sidechain to form a C-22 alcohol; and subjecting the C-22 alcohol to $SO_2$ extrusion and Swern oxidation to form the C-22 aldehyde.

The reaction of the C-22 aldehyde and the phenyl sulfone reaction yields a hydroxyl-protected-25-ene-vitamin D, which is reduced, isomerized and deprotected to yield a 25-ene-vitamin $D_2$. If 24-hydroxy compounds are desired the 25-ene-vitamin $D_2$ is further incubated with hepatoma cells to yield the 24-hydroxy-25-ene-vitamin $D_2$.

It is noted that the starting material for the method of the present invention is suitably a vitamin D, a previtamin D, a cholesterol or an ergosterol.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWING(S)

The preferred exemplary embodiment of the present invention will hereinafter be described in conjunction with the appended drawing wherein like designations refer to like elements throughout and in which.

DETAILED DESCRIPTION OF THE INVENTION

Figure 1:
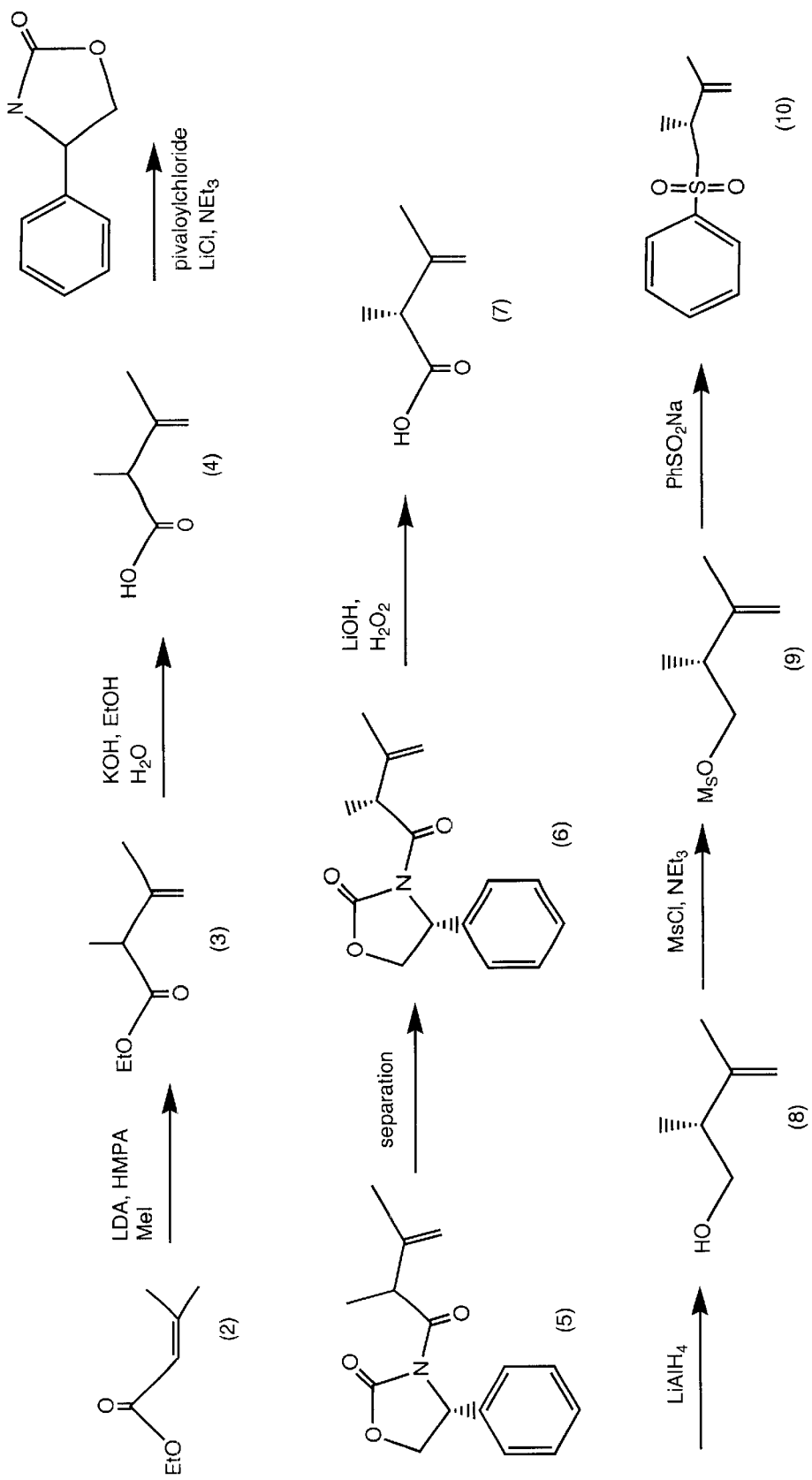
FIG. 1 is a reaction scheme for preparation of the phenyl sulfone to attach the appropriate sidechain to the vitamin D of FIG. 2.

The present invention relates to methods of preparing a novel class of vitamin D compounds which have highly advantageous biological activity. Specifically, the method of the present invention is most particularly adapted for making hydroxy-25-ene-vitamin D compounds. Accordingly, the present invention will now be described in detail with respect to such endeavors; however, those skilled in the art will appreciate that such a description of the invention is meant to be exemplary only and should not be viewed as limitative on the full scope thereof.

The method of the present invention is characterized by yielding prodrugs of 10α,24-dihydroxylated vitamin D compounds as they are hydroxylated in vivo at the 24-position or the 1α-position to become active forms of vitamin D. As prodrugs, these compounds in effect circumvent the first pass concern over intestinal vitamin D receptor binding which mediates intestinal calcium absorption, thereby resulting in reduced or no hypercalcemia compared with similar dosing with known active vitamin D compounds such as 1α,25-dihydroxyvitamin $D_3$.

As used herein, the terms "calcemic activity" and "calcemic action" refer to the well-known ability of vitamin D compounds to raise blood calcium levels by virtue of their stimulation of intestinal calcium absorption (calcium transport) and of calcium resorption from bone (bone mobilization). Also, as used herein, the term "lower" as a modifier for alkyl, alkenyl, fluoroalkyl, fluoroalkenyl or cycloalkyl is meant to refer to a straight chain, branched chain or cyclic, saturated or unsaturated hydrocarbon radical having 1 to 4 carbon atoms. Specific examples of such hydrocarbon radicals are methyl, ethyl, propyl, isoprophyl, butyl, isobutyl, t-butyl, ethenyl, propenyl, butenyl, isobutenyl, isopropenyl, formyl, acetyl, propionyl, butyryl or cyclopropyl. As used herein, the term "hydrocarbon moiety" refers to a straight chain, branched chain or cyclic, saturated or unsaturated $C_1$–$C_4$ hydrocarbon radial, e.g., a lower alkyl, a lower alkenyl or a lower cycloalkyl. Also, the term "equivalent position," as used herein, e.g., C-24 or equivalent position, is meant to refer to a particular carbon in the C-17 side chain of a vitamin D compound wherein that carbon would be the C-24 carbon but for homologation of the side chain. The term "hydroxyl-protected" is meant to refer to an oxygen that is bonded to a protecting group, e.g., TBDMSCl;, that remains inert unless specifically converted to a hydroxyl group.

Structurally, the key feature of the compounds in accordance with the present invention having the desirable biological attributes is that their C-17 side chain has a double bond at the C-25 or equivalent position. In addition, the side chain is optionally extended by insertion of one or two methylene ($CH_2$—) or methyne ($CH$=) units. Thus, the vitamin D compounds of the present invention are suitably represented by general formula (I):

Wherein D is a moiety which is $D^1$, $D^2$ or $D^3$ in which $D^1$ is a vitamin D, $D^2$ is a previtamin D, and $D^3$ is a cholesterol or a ergosterol moiety described hereinafter as formulas (II), (III) and IV), respectively, and wherein Z represents a C-17 sidechain which is a saturated or unsaturated, substituted or unsubstituted, straight-chain, branched-chain or cyclic $C_4$–$C_{18}$ hydrocarbon group in which the C-25 position or the equivalent position has a double bond, and in which the C-24 or equivalent position is bonded by one single C—C bond to a lower alkyl, lower fluoroalkyl, lower alkenyl or lower fluoroalkenyl, and by a second bond to a hydrogen or a hydroxyl group.

It is noted that previtamin D compounds are the thermal isomers of the corresponding vitamin D compounds, e.g., previtamin $D_3$ is the thermal isomer of vitamin $D_3$, and exists in thermal equilibrium with same. Cholesterol and ergosterol compounds are the well-known precursors in the biosynthesis of vitamin D compounds.

Preferably, $D^1$—Z is a vitamin D analog characterized by the general formula (II):

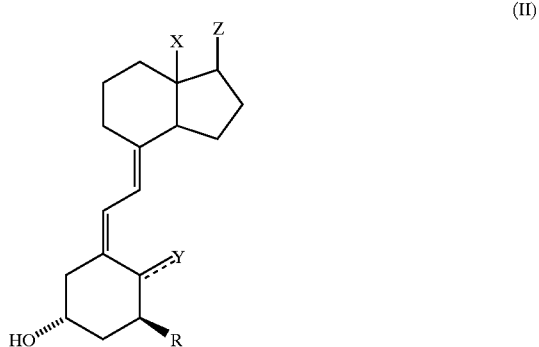

wherein Z is as described above; Y is a methylene group if the bond to Y is a double bond or a methyl group or hydrogen if the bond to Y is a single bond, i.e., when Y is hydrogen, the compound of formula (II) is a 19-nor compound; R is hydrogen or hydroxyl such that when R is hydrogen, Z is a side chain wherein the C-24 or equivalent position is hydroxylated; and when R is hydroxyl, the C-24 or equivalent position of the Z side chain is not hydroxylated; and X is hydrogen, lower alkyl or lower fluoroalkyl.

Another example of $D^1$—Z compound is represented by formula (IIA), below:

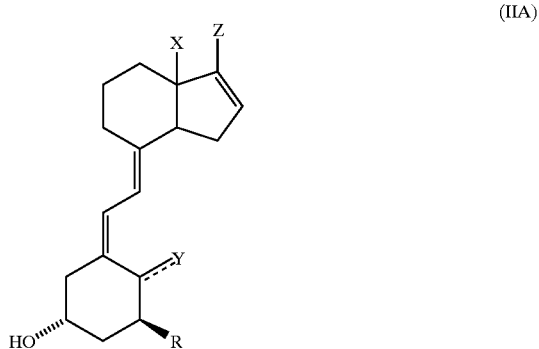

wherein X, Y, R and Z are as defined above.

$D^2$—Z is a previtamin D analog represented by the general formula (III):

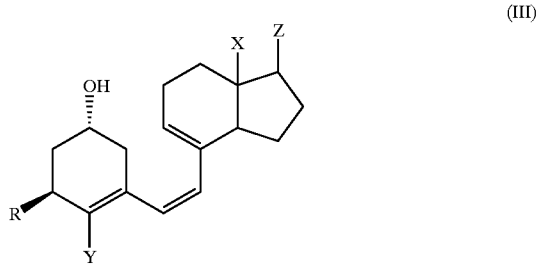

wherein Z, R and X are as described above, and Y is hydrogen or a methyl group.

$D^3$—Z is a cholesterol or ergosterol analog characterized by the general formula (IV):

(IV)

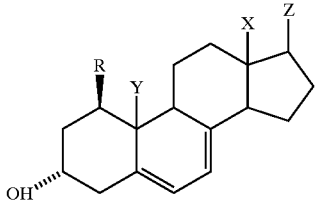

wherein Z, R and X are as described above, and Y is hydrogen or a methyl group.

Preferably, Z, the C-17 side chain, is represented by the general formula (VA):

(VA)

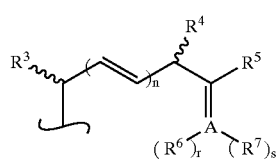

wherein n is an integer which is 1 or 2; $R^3$ is hydrogen, lower alkyl, lower alkenyl, lower fluoroalkyl or lower fluoroalkenyl; $R^4$ and $R^5$ are independently lower alkyl, lower fluoroalkyl, lower alkenyl or lower fluoroalkenyl; A is carbon, oxygen, sulfur or nitrogen; r is 1 and s is zero when A is nitrogen; r and s are zero when A is sulfur or oxygen; and $R^6$ and $R^7$ are independently hydrogen, lower alkyl, lower alkenyl, lower fluoroalkyl or lower fluoroalkenyl.

For example, Z includes a side chain wherein A is carbon, r and s are 1, and n is 1 and which is represented by formula (VB):

(VB)

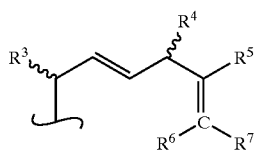

wherein $R^3$, $R^6$ and $R^7$ are independently hydrogen, lower alkyl, lower fluoroalkyl, and lower fluoroalkenyl, and $R^4$ and $R^5$ are lower alkyl, lower fluoroalkyl, lower alkenyl or lower fluoroalkenyl.

Also, Z includes a side chain represented by formula (VC):

(VC)

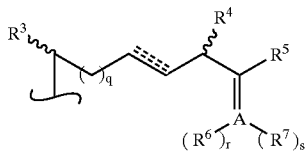

wherein a dotted line along the side chain represents an optional additional C—C bond; q is zero or an integer which is 1 or 2; $R^3$ is hydrogen, lower alkyl, lower alkenyl, lower fluoroalkyl or lower fluoroalkenyl; A is carbon, oxygen, sulfur or nitrogen; r is 1 and s is zero when A is nitrogen, r and s are zero when A is oxygen or sulfur; $R^6$ and $R^7$ are independently hydrogen, lower alkyl, lower alkenyl, lower fluoroalkyl or lower fluoroalkenyl. As to the optional C—C bond, for example, if q=0, the bond between C-22 and C-23 may be single, double or triple. As to the group to which q refers, this is a —$CH_2$— group.

For example, Z includes a side chain wherein q is zero, A is carbon and which is represented by formula (VD):

(VD)

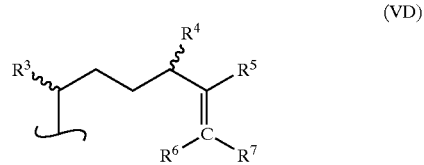

wherein $R^3$, $R^6$ and $R^7$ are independently hydrogen, lower alkyl, lower fluoroalkyl, lower alkenyl and lower fluoroalkenyl, and $R^4$ and $R^5$ are independently lower alkyl, lower fluoroalkyl, lower alkenyl or lower fluoroalkenyl.

Preferably, Z is also a side chain represented by formula (VE):

(VE)

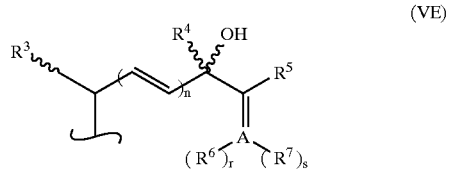

wherein n is an integer which is 1 or 2; $R^3$ is hydrogen, lower alkyl, lower fluoroalkyl, lower alkenyl or lower fluoroalkenyl; $R^4$ and $R^5$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is oxygen or sulfur; and $R^6$ and $R^7$ are independently hydrogen, lower alkyl, lower fluoroalkyl, lower alkenyl or lower fluoroalkenyl.

For example, Z includes a side chain when n is 1, A is carbon, r and s are 1 and $R^3$, $R^4$, $R^5$, $R^6$ and $R^7$ are as described above and represented by formula (VF):

(VF)

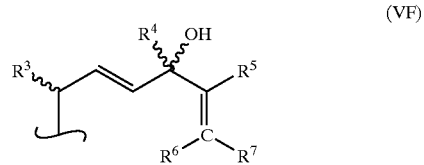

Also, Z includes a side chain represented by formula (VG):

(VG)

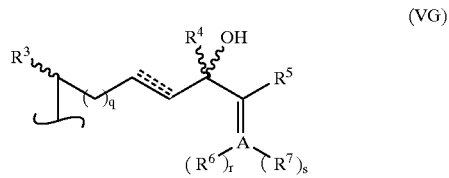

wherein a dotted line along the side chain represents an optional additional C—C bond; q is zero or an integer which is 1 or 2; $R^3$ is hydrogen, lower alkyl, lower fluoroalkyl, lower alkenyl or lower fluoroalkenyl; $R^4$ and $R^7$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; $R^9$ and $R^{10}$ are independently hydrogen, lower alkyl, lower alkenyl, lower fluoroalkyl or lower fluoroalkenyl. As to the optional additional bonds, for example, when q=0, there may be a double bond between C-22 and C-23.

For example, Z includes a side chain wherein q is zero, A is carbon, r and s are 1, $R^3$, $R^4$, $R^5$, $R^6$ and $R^7$ are as described above and represented by formula (VH):

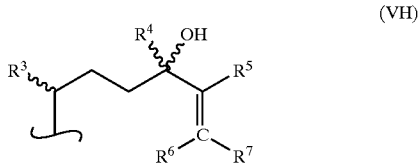

(VH)

Preferred among the compounds of formula (I) are the 1α-hydroxylated or the 24-hydroxylated compounds which are prodrugs for 1α,24-dihydroxylated vitamin D. Examples of the compounds of formula (I) are:

1α-hydroxy-25-ene-vitamin $D_2$
1α-hydroxy-25-oxo-vitamin $D_2$
24-hydroxy-25-ene-vitamin $D_2$
24-hydroxy-25-oxo-vitamin $D_2$ Preferred among the compounds of formula (III) are the 1-hydroxy previtamin D compounds which are prodrugs and isomers for 1α, 24-dihydroxylated vitamin D. Examples of the compounds of formula (III) are:

1α-hydroxy-25-ene-previtamin $D_2$
1α-hydroxy-25-oxo-previtamin $D_2$
24-hydroxy-25-ene-previtamin $D_2$
24-hydroxy-25-oxo-previtamin $D_2$ Preferred among the compounds of formula (IV) are the 1α-hydroxylated precursor compounds of vitamin D compounds, i.e., 1α-hydroxylated cholesterol or ergosterol compounds, which are also prodrugs for 1α, 24-dihydroxylated vitamin D. Examples of the compounds of formula (IV) are:

1α-hydroxy-24-methyl-25-ene-cholesterol
1α-hydroxy-24-methyl-25-oxo-cholesterol
1α-hydroxy-25-oxo-ergosterol
24-hydroxy-25-ene-cholesterol
24-hydroxy-25-ene-ergosterol
24-hydroxy-25-oxo-cholesterol
24-hydroxy-25-oxo-ergosterol Among those compounds of the present invention that have chiral centers, e.g., in the C-17 sidechain at C-20 or C-24, it is understood that both diastereomers (e.g., R and S) and the mixture thereof are within the scope of the present invention.

In the following description of the method of the invention, process steps are carried out at room temperature (RT) and atmospheric pressure unless otherwise specified.

The compounds of formula (I) may be prepared by the exemplary reaction process depicted in FIG. 1. The synthesis is characterized by coupling the appropriate, and separately synthesized, side chain unit to the desired preformed vitamin D nucleus bearing a displacable group at C-22. The required side chain is prepared as a phenyl sulfone derivative. Specifically, the method of the present invention for preparing the 1α-hydroxylated compounds entails using vitamin D as a starting material, hydroxylating the carbon-1 position and protecting same, and then, forming 1α-hydroxy-25-ene-vitamin D. For preparing the 24-hydroxylated compounds, the starting material is also vitamin D and a 25-ene-vitamin D compound is formed, which is then hydroxylated in the 24-position by, e.g., biological generation.

Figure 2A:
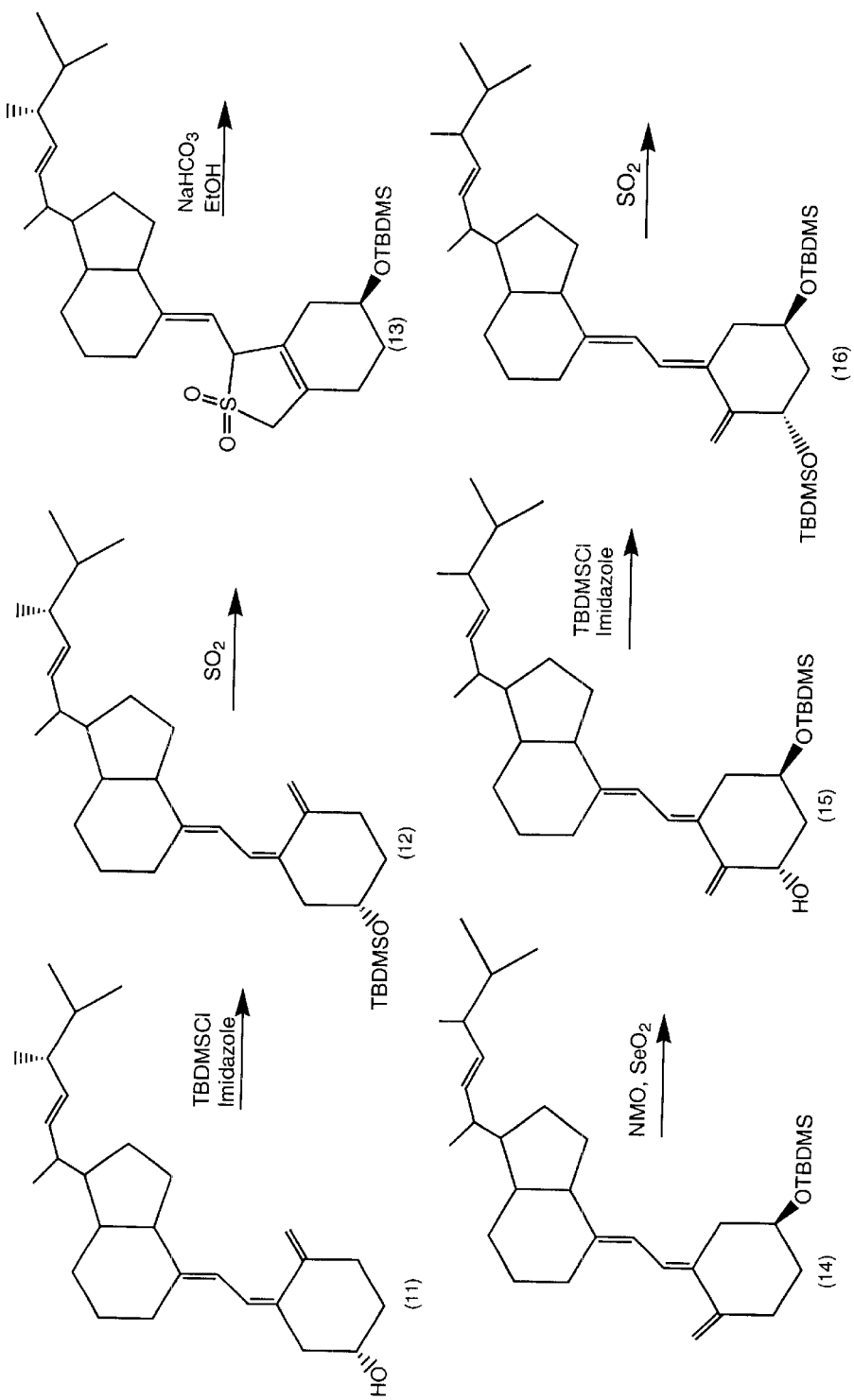
FIGS. 2A–2B is a reaction scheme for the preparation of 1α-hydroxy-25-ene-vitamin $D_2$ in accordance with the present invention.
Figure 2B:
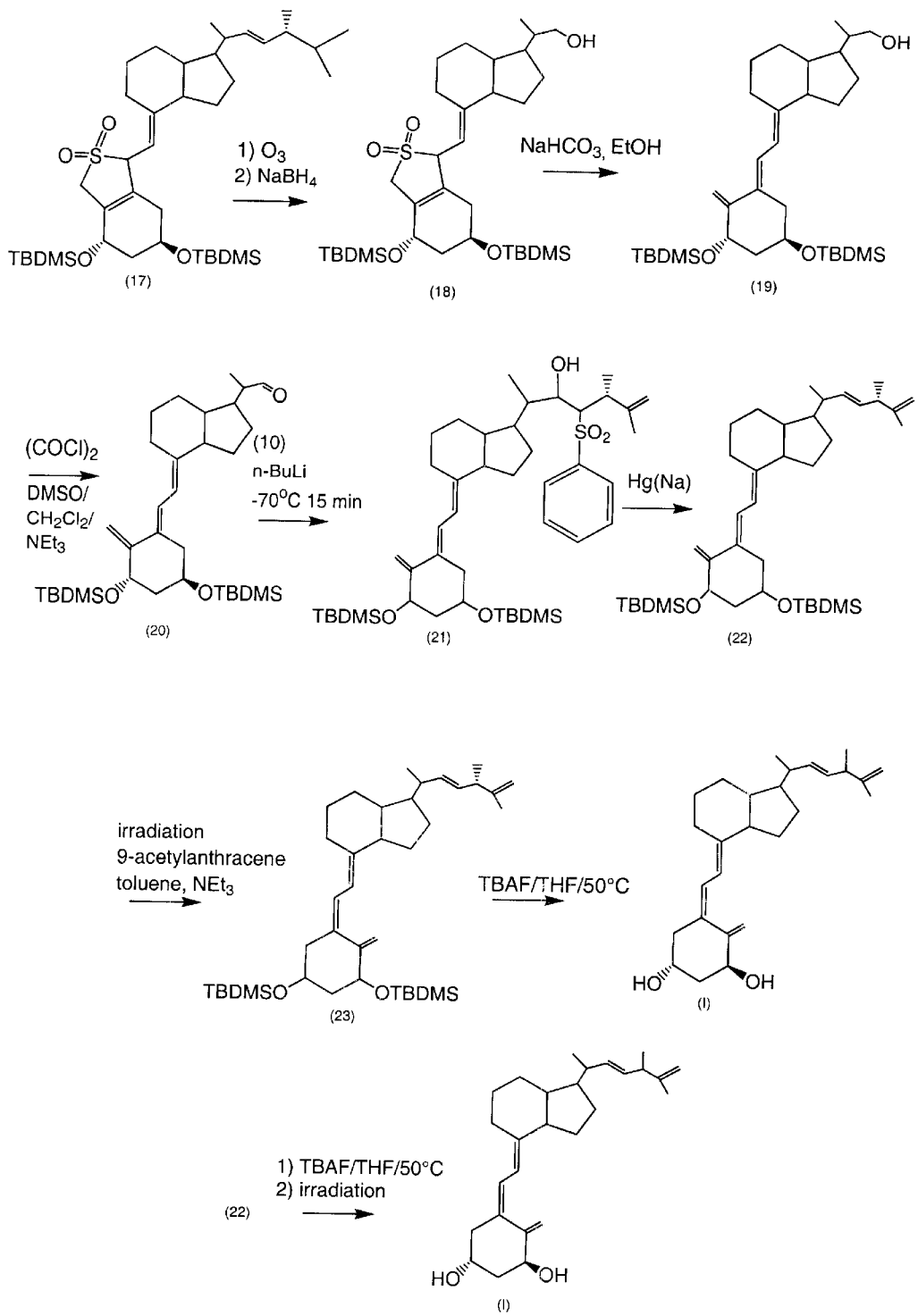

Reference is now made to FIGS. 2A–2B which is an exemplary reaction scheme for the synthesis of 1α-hydroxy-25-ene-vitamin $D_2$. The hydroxyl functionality at the C-3 position of vitamin $D_2$ (11) is protected with t-butyldimethylsilyloxychloride (TBDMSCl) in the presence of imidazole to form the C-3-protected product (12), which is then reacted with $SO_2$, affording the adduct intermediate (13). The adduct (13) is then subjected to $SO_2$ extrusion (sodium bicarbonate ($NaHCO_3$)/ethanol (EtOH)) to yield the trans-isomer (14) of (12). The trans-isomer (14) is hydroxylated ($NMO/SeO_2$) in the C-1 position to yield (15). The hydroxyl functionality at C-1 is then protected (TBDMSCl) and reacted with $SO_2$ to form the adduct (17). Ozonolysis and reduction affords a C-22 alcohol (19) (see, Manchand et al., 60 *J. Org. Chem.* (1995) 6574, incorporated herein by reference). $SO_2$ extrusion ($NaHCO_3$; EtOH), and subsequent oxidation using the known Swern oxidation $((COCl)_2)_2$; DMSO) affords the C-22 aldehyde (20). The side chain is introduced by reaction of aldehyde (20) with the appropriate phenyl sulfone (10), followed by appropriate reduction, deprotection and isomerization to yield the 1α-hydroxy-25-ene-vitamin $D_2$ compound (1).

The compounds of formula (III) may be generally prepared by the process exemplified in FIG. 1 wherein the previtamin starting materials can be prepared by the exemplary reaction processes given in, e.g., U.S. Pat. No. 5,252,191 issued to Pauli et al.; U.S. Pat. No. 5,025,783 issued to Coethals et al. U.S. Pat. No. 4,388,243, all of which are incorporated herein by reference. The 19-nor compounds of formula (I) may also be prepared generally by the exemplary reaction process given herein, the starting material for which may be prepared by the process given in U.S. Pat. No. 5,710,294 incorporated herein by reference. The process given in FIG. 1 is also suitable for preparation of compounds of formula (IV) wherein the cholesterol or ergosterol starting materials are commercially available.

To form the appropriate phenyl sulfone (10), reference is now made to FIG. 1 which illustrates a reaction scheme therefor. Ethyl dimethylacrylate (2) undergoes methylation and double bond isomerization to the C-3 position. The ether group is converted to an alcohol group to form an acid (4). The acid (4) is converted to the oxazolidinone isomers (5) and separated to yield the desired isomer (6). Oxazolidinone (6) is converted to a butanoic acid-3-ene (7). The carbonyl group of this acid (7) is removed to yield the alcohol (8). The alcohol (8) is reacted to replace the alcohol group to yield a mesylate (9). The mesylate (9) is then converted to a phenyl sulfone group to yield R-(2,3-dimethyl-3-butene-1-yl) phenyl sulfone (10).

Certain of the compounds described herein and methods for making therefor are described in Calverley, *Tetrahedron* 51 (1987) 1609; Manchand et al., *J. Org. Chem.* 60 (1995) 6574; Walba et al., *J. Org. Chem.* 53 (1988) 1046; Smith III et al., *J. Am. Chem. Soc.* 103 (1981) 1996, all of which are incorporated herein by reference.

Figure 3:
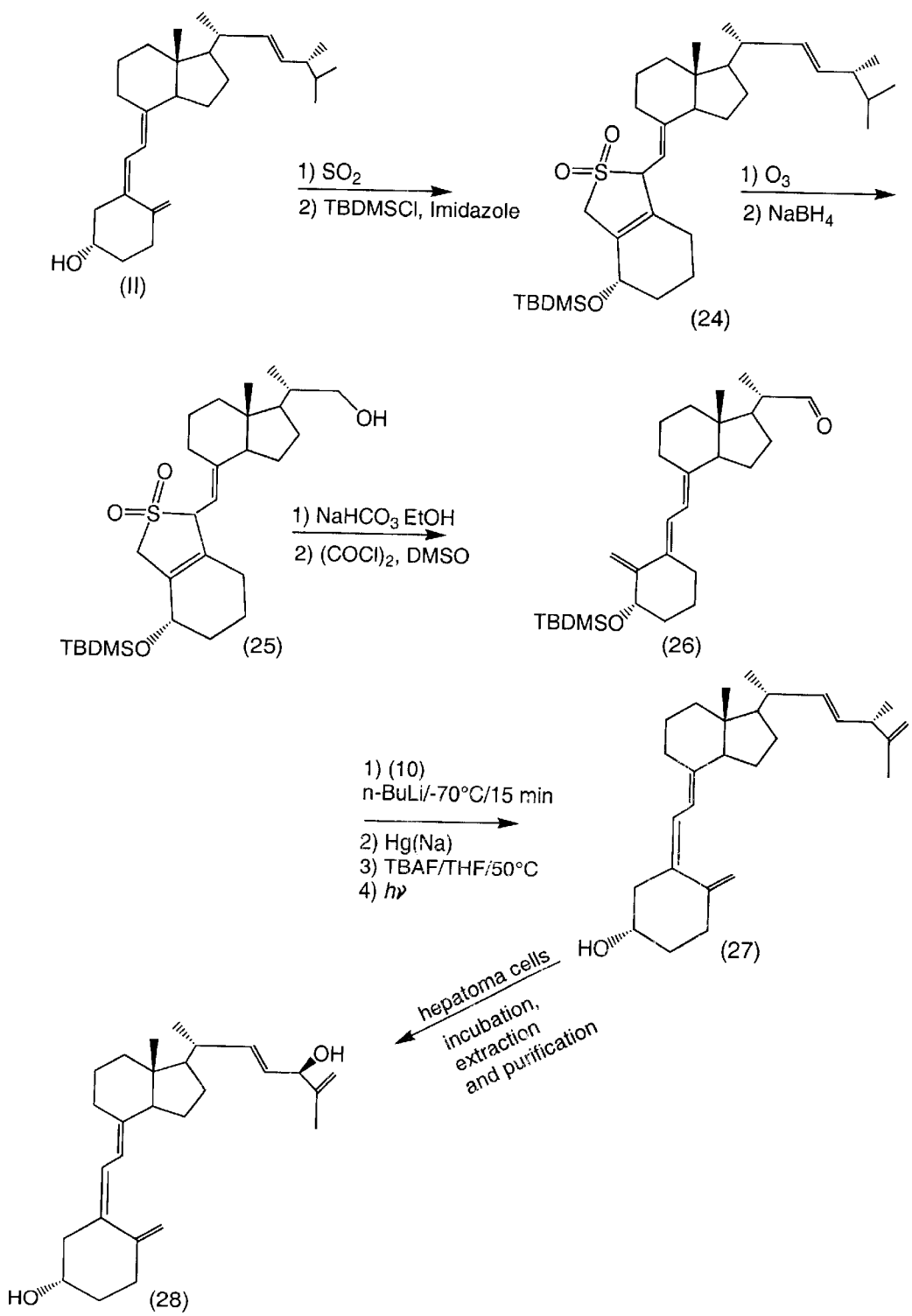
FIG. 3 is a reaction scheme for the preparation of 24-hydroxy-25-ene-vitamin $D_2$ in accordance with the present invention.

The compounds of formula (II) wherein the side chain is represented by formulas (IIC) or (IIE) may be prepared by the exemplary reaction process depicted in FIG. 3. Specifically, a method of preparing 24-hydroxy-25-ene-vitamin $D_2$ entails using vitamin $D_2$ as a starting material, eliminating the C-1 hydroxylation and protection steps of the process of FIG. 2A, and forming the 25-ene-vitamin $D_2$, followed by incubating the 25-ene-vitamin $D_2$ with, e.g., cultured human hepatoma cells, HEP3B or HEPG3, to yield the metabolite 24(S)-hydroxy-25-ene-vitamin $D_2$ which is then isolated, purified by high pressure liquid chromatography.

As seen in FIG. 3, and similar to FIGS. 2A–2B, vitamin $D_2$ (11) is reacted with $SO_2$ and the hydroxyl functionality at C-3 is protected with t-butyldimethylsilyloxychloride affording the adduct intermediate (24). Ozonolysis and reduction affords the C-22 alcohol (25). $SO_2$ extrusion, and subsequent oxidation using the known Swern oxidation affords the aldehyde (26). The side chain is introduced by reaction of aldehyde (9) with the appropriate phenyl sulfone reagent to yield the 25-ene-vitamin $D_2$ compound (27) with appropriate reduction, isomerization and deprotection. The 25-ene-vitamin $D_2$ is then incubated with human hepatoma cells to yield the 24-hydroxy-25-ene-vitamin $D_2$ (28) which is extracted, and purified into the 24(S)-hydroxy diastereomer.

The present invention is further explained by the following examples which should not be construed by way of limiting the scope of the present invention.

$^1$H-NMR spectra were recorded on a Varian VXR-300. Chemical shirfts are denoted in δ units (ppm) relative to TMS. For HPLC analysis, a platinum EPS C18 150×4.6 mm column was used with a liquid phase of $CH_3CN$-0.1% COOH 70:30, with a detection wavelength of 265 nm, a flow of 1 mL/min and a temperature of 22° C. Melting points were determined on a Mettler FP-2 melting point apparatus equipped with a Mettler FP-21 microscope.

EXAMPLE 1

Synthesis of 1α-hydroxy-25-ene-vitamin D
Preparation of R-(2,3-Dimethyl-3-butene-1-yl) phenyl sulfone (10)

To a solution of 110 mL diisopropylamine in 750 mL tetramethylfuran (THF) was 315 mL 2.5 N n-butyllithium (n-BuLi) at a temperature between −25° C. and −10° C. The mixture was cooled to −70° C., and 150 mL HMPA was added dropwise, and the mixture stirred for an additional hour at this temperature. After the dropwise addition of 100 g ethyl dimethylacrylate (2) in 100 mL THF, the mixture was stirred for 2 hr at 70° C. followed by the addition of 60 mL methyl iodide (MeI), maintaining a temperature below −50° C. The reaction mixture was allowed to reach RT overnight and quenched by the addition of 400 mL saturated $NH_4Cl$ solution. The layers Were separated and the aqueous phase extracted with ether-hexane 1:1 (400 mL and 300 mL). The combined organic layers were washed with 0.5 N HCl, saturated $NaHCO_3$ solution, brine and dried ($Na_2SO_4$). Evaporation of the solvents afford 113 g of crude product (3) as an oil. NMR ($CDCl_3$): δ: 1.2 (m, 6H); 1.65 (s, 3H); 3.15 (q, 1H); 4.05 (q, 2H); 4.75 (s, 2H).

The oil (3) was stirred in 800 mL EtOH-water 1:1 with 52 g KOH for 4 days at RT. After the mixture had been concentrated, it was washed with ether (2×100 mL), acidified and extracted with ether-hexane 1:1 (4×300 mL). The combined organic layers were washed with brine, dried ($Na_2SO_4$), and the solvents evaporated to yield 74 g of the acid compound (4). NMR ($CDCl_3$): δ: 1.3 (d, 3H); 1.8 (s, 3H); 3.2 (q, 1H); 4.9 (s, 2H); 11 (broad s, 1H).

A solution of 71.5 g of compound (4) and 176 triethylamine ($NEt_3$) in 1.25 L THF was mechanically stirred and cooled to −40° C. To the solution was added dropwise 83 g pivaloylchloride. The resulting white suspension was stirred for 1.5 hr while the temperature reached −8° C., and was recooled to −50° C. followed by the addition of 29.5 g LiCl and 102.2 g S(+)-phenyl oxazolidone. The mixture was allowed to reach RT overnight, poured into 1 L water, and extracted with ethyl acetate (EtOAc) (2×0.5 L). The combined organic layers were washed with brine, dried ($Na_2SO_4$), and evaporated. Bulb to bulb distillation afforded 136 g (75% relative to ethyl dimethylacrylate) of oxazolidinone products (5) as a thick yellow oil. NMR($CDCl_3$): δ: 1.2 (d, 3H); 1.65 and 1.8 (2s, 3H); 4.2 (dd, 1H); 4.35 (m, 1H); 4.45,4.75, 4.8, 4.85 (4s, 2H); 4.65 (m, 1H); 5.45 (m, 1H); 7.3 (m, 5H).

The oxazolidinones (5) were chromatographed using 8.6 kg silica and $CH_2Cl_2$ as eluent. Collection of the appropriate fraction ($R_f$=0.5) afforded 581 g of the desired isomer (6). NMR($CDCl_3$): δ: 1.2 (d, 3H); 1.8 (s, 3H); 4.2 (dd, 1H); 4.4 (q, 1H); 4.65 (q, 1H); 4.8 (s, 1H); 4.85 (s, 1H); 5.4 (dd, 1H); 7.3 (m, 5H).

61.6 g of the oxazolidinone (6) in 1 L THF was cooled to 0° C., and 21 g $LiOH.H_2O$ in 300 mL was added dropwise, followed by 95 mL 30% $H_2O_2$. The mixture was allowed to slowly reach RT overnight, and was recooled to 0° C. $Na_2SO_3$ (105 g) was added, followed by 200 mL water and 100 mL ether to achieve phase separation. The aqueous phase was washed with hexane, acidified and extracted with ether (3×250 mL, 150 mL). The ether layers were dried ($Na_2SO_4$), and the solvent evaporated, yielding 23 g of the acid (7). A solution of this acid in 100 mL THF was added dropwise to a mixture of 8.2 g $LiAlH_4$ in 150 mL THF with cooling. After the mixture had reached RT, it was refluxed for 1 hr, cooled to 0° C., and quenched with a $Na_2SO_4$ solution dropwise. The resulting solid was filtered and washed with THF. The combined THF layers containing the alcohol (8) were cooled to 0° C., followed by the introduction of 42 mL $NEt_3$ and 20 mL methane sulfonylchloride dropwise. The mixture was left at RT overnight, poured into 300 mL water, and extracted with EtOAc (2×300 mL). The combined organic layers were washed with brine, dried and evaporated. Bulb to bulb distillation afforded 4.9 g of a mesylate (9) as a colorless oil (11% relative to oxazolidinone). NMR($CDCl_3$): δ: 1.1 (d, 3H); 1.7 (s, 3H); 2.55 (m, 1H); 2.95 (s, 3H); 4.1 (m, 1H); 4.75 (s, 1H); 4.85 (s, 1H).

A solution of 4.9 g of (9), 5.8 g sodium benzenesulfinate ($PhSO_2Na$) and 4.1 g NaI in 50 mL dimethylfuran (DMF) was stirred at 50° C. for 4 days. The mixture was poured into 100 mL ice-water and extracted with EtOAc (2×100 mL). The combined organic layers were washed with brine (2×50 mL), dried and evaporated. Bulb to bulb distillation afforded 5.6 g (90%) of the product R-(2,3-methyl-3-butene-1-yl) phenyl sulfone (10) as a colorless oil. NMR($CDCl_3$): δ:1152 (d, 3H); 1.6 (s, 3H); 2.7 (m, 1H); 3 (dd, 1H); 3.2 (dd, 1H); 5.65 (s, 2H); 7.5 (m, 3H); 7.85 (d, 2H).

Preparation of 1(S),3(R)-Bis-(t-butyldimethylsilyloxy)-20 (S)-formyl-9,10-secopregna-5(E),7,(E),10(19)-tiene (20)

57.5 g (145 mmol) vitamin $D_2$ (11) and 16.1 g imidazole in 500 mL $CH_2Cl_2$ was cooled to −5° C. To this mixture was added 28.9 g TBDMSCl portionswise. The temperature was allowed to reach RT and left at this temperature for 5 hr. The reaction was monitored by thin layer chromatography (TLC) (silica, $CH_2CL_2$), poured into water, and the layers separated. The aqueous phase was extracted with $CH_2Cl_2$, and the combined organic layers washed with water and brine. Drying ($Na_2SO_4$) and evaporation afforded the C-3 protected compound (12) as a yellow oil. NMR($CDCl_3$): δ: 0 (s, 6H); 0.5 (s, 3H); 0.9 (m, 18H); 1 (d, 3H); 1.1–2.4 (m, 20H); 2.75 (d, 1H); 3.75 (m, 1H); 4.7 (s, 1H); 4.95 (s, 1H); 5.15 (m, 2H); 5.95 (d, 1H); 6.1 (d, 1H).

The oil (12) was dissolved in 100 mL ether and added to 100 mL $SO_2$ at −50° C. The mixture was refluxed for 2 hr at −10° C., and the $SO_2$ evaporated under an argon atmosphere, affording the protected adduct compound (13) as an off-white solid. NMR(CDCl$_3$): δ: 0 (s, 6H); 0.6, 0.65 (2s, 3H); 0.9 (m, 18H); 1 (d, 1H); 1 (d, 3H); 1.1–2.2 (m, 20H); 2.5 (m, 1H); 3.6 (broad s, 2H); 3.95 (m, 1H); 4.4–4.75 (m, 2H); 5.15 (m, 2H).

The off-white residual solid (13) was dissolved in 675 mL 96% ethanol; 75 g NaHCO$_3$ was added and the mixture refluxed until LC (silica, CH$_2$Cl$_2$) displayed disappearance of starting material (4 hr). The reaction was cooled to 0° C., hexane (700 mL) and EtOAc (700 mL) were added, and the mixture was filtered over Celite™. Evaporation afforded 73 g of the trans compound (14) as a yellow oil. NMR(CDCl$_3$): δ: 0 (s, 6H); 0.5 (s, 3H); 0.9 (m, 18H); 1 (d, 3H); 1.1–2.3 (m, 18H); 2.5 (m, 1H); 2.65 (dd, 1H); 2.85 (dd, 1H); 3.85 (m, 1H); 4.65 (s, 1H); 4.95 (s, 1H); 5.2 (m, 2H); 5.85 (d, 1H); 6.5 (d, 1H).

The oil (14) was dissolved in 600 mL CH$_2$Cl$_2$. After the addition of 36.3 g NMO, the solution was dried over Na$_2$SO$_4$, filtered and heated to reflux. To this solution, a solution of 16.2 g SeO$_2$ in 375 mL of hot MeOH was added within 5 min. The heating was continued for 70 min, the mixture cooled and poured into 700 mL water. The phases were separated, and the aqueous phase extracted with CH$_2$Cl$_2$ (3×100 mL). The combined organic layers were washed with brine, dried (Na$_2$SO$_4$), and filtered through silica. Evaporation afforded 73 g yellow oil which was chromatographed using 800 g silica, 5 L 2.5% EtOAc in hexane and 2 L 75% EtOAc in hexane. The latter 2 L were collected and evaporated to afford 55.6 g of the C-1 protected compound (15) as a yellow oil. NMR(CDCl$_3$): δ: 0 (s, 6H); 0.5 (s, 3H); 0.9 (m, 16H); 1 (d, 3H); 1.1–2.0 (m, 18H); 2.35 (d, 1H); 2.5 (d, 1H); 2.8 (d, 1H); 4.15 (m, 1H); 4.9 (s, 1H); 5.05 (s, 1H); 5.8 (d, 1H); 6.45 (d, 1H).

55.6 g of (15) was dissolved in 700 mL CH$_2$Cl$_2$, 11.8 g imidazole added and upon cooling to −5° C., 21.3 g TBDM-SCl was added. The mixture was allowed to reach RT overnight and poured into 500 mL water. The layers were separated, the aqueous phase extracted with CH$_2$Cl$_2$ and the combined organic layers washed with water and brine. Drying (Na$_2$SO$_4$) and evaporation of the solvent afforded 56.6 g of a solid. This solid was dissolved in 250 mL hot EtOAc, and 300 mL hot MeOH was added. Crystallization occurred within 10 min and the mixture was cooled to 0° C. The solid was isolated and washed with a mixture of MeOH and EtOAc. This afforded 29.8 g (325 relative to (11)) of the α-isomer (16) as a white crystalline solid. NMR(CDCl$_3$): δ: 0 (s, 12H); 0.5 (s, 3H); 0.9 (m, 27H); 1 (d, 3H); 1.1–2.0 (m, 16H); 2.25 (d, 1H); 2.5 (dd, 1H); 2.8 (d, 1H); 4.15 (m, 1H); 4.5 (m, 1H); 4.9 (s, 1H); 4.95 (s, 1H); 5.15 (m, 2H); 5.8 (d, 1H); 6.4 (d, 1H).

Compound (16) (9 g) was dissolved in a mixture of 30 mL SO$_2$ and 30 mL CH$_2$Cl$_2$, and refluxed for 1 hr. The solvents were evaporated and 10 g of adduct product (17) was obtained as a white solid. NMR(CDCl$_3$): δ: 0 (s, 12H); 0.5 (s, 3H); 0.9 (m, 27H); 1 (d, 3H); 1.1–2.2 (m, 18H); 2.55 (m, 1H); 3.6 (d, 1H); 3.9 (d, 1H); 4.15 (m, 1H); 4.35 (m, 1H); 4.6–4.8 (m, 2H); 5.15 (m, 2H).

Ozonolysis of this 10 g of solid (17) was carried out at −65° C. in 100 mL CH$_2$Cl$_2$ and 50 mL MeOH, and monitored by TLC (silica, CH$_2$Cl$_2$). Subsequently, 2 g NaBH$_4$ was added, the reaction mixture allowed to reach 10° C. and poured into 150 mL acetate buffer of pH 4.3 (11 g potassium acetate (KOAc)). The mixture was extracted with hexane (2×60 mL), the organic layers washed with brine and dried (Na$_2$SO$_4$). Evaporation afforded the crude product of adduct alcohol (18) as a yellow oil, which was dissolved in 150 mL EtOH (96%). Upon the addition of 12 g NaHCO$_3$, the mixture was refluxed in an argon atmosphere until TLC (silica, CH$_2$Cl$_2$) displayed the absence of starting material (2 hr). After cooling, 200 mL hexane and 100 mL EtOAc were added, followed by Na$_2$SO$_4$ and Celite™. The mixture was filtered over Celite™ and the solvents evaporated to afford 11 g of a solidifying yellow oil. Column chromatography (silica, CH$_2$Cl$_2$) provided 5.2 g (64%) of the trans-isomer of the alcohol compound (19). NMR(CDCl$_3$): δ: 0 (s, 12H); 0.5 (s, 3H); 0.85 (s, 9H); 0.9 (s, 9H); 1 (d, 3H); 1.1–2 (m, 14H); 2.25 (d, 1H); 2.5 (dd, 1H); 2.85 (d, 1H); 3.35 (m, 1H); 3.6 (m, 1H); 4.2 (m, 1H); 4.5 (m, 1H); 4.9 (s, 1H); 4.95 (s, 1H); 5.8 (d, 1H); 6.4 (d, 1H).

To a solution of 0.124 mL oxaloylchloride in 30 mL CH$_2$Cl$_2$ at −70° C. was added a solution of 0.26 mL dimethylsulfoxide (DMSO) in 10 mL CH$_2$Cl$_2$ over a period of 15 min keeping the temperature below −65° C., and kept at −60° C. for 10 min. The mixture was recooled to −70° C. and 710 mg alcohol (19) in 30 mL CH$_2$Cl$_2$ was added in 10 min, keeping the temperature below −60° C. After 20 min at a temperature between −60° C. and −50° C., the turbid mixture was recooled to −70° C., and 0.88 mL NEt$_3$ was added at once. The temperature was allowed to reach RT and the clear solution poured into 50 mL water. The phases were separated, the water layer extracted with CH$_2$Cl$_2$ (50 mL), the combined organic layers washed with brine and dried (Na$_2$SO$_4$). After removal of the solvent, the residue ws purified by column chromatography (silica, CH$_2$Cl$_2$) yielding 630 mg (89%) of 1(S),3(R)-bis-(t-butyldimethysilyloxy)-20(S)-formyl-9,10-secopregna-5(E), 7(E),10(19)triene (20) as a white crystalline solid. NMR (CDCl$_3$): δ: 0 (s, 12H); 0.5 (s, 3H); 0.85 (s, 9H); 0.9 (s, 9H); 1.1 (d, 3H); 1.2–2.4 (m, 15H); 2.5 (dd, 1h); 2.85 (d, 1H); 4.2 (m, 1H); 4.5 (m, 1H); 4.9 (s, 1H); 4.95 (s, 1H); 5.8 (d, 1H); 6.4 (d, 1H); 9.55 (d, 1H). MS m/z (M$^+$).

Preparation of 1α-hydroxy-25-ene-vitamin D$_2$ (1)

A solution of 1.36 g the phenyl sulfone (10) in 40 mL THF was cooled to −70° C.; 2.4 mL 2.5 M n-BuLi was added, and the mixture stirred at the same temperature for 1 hr. 850 mg of aldehyde (20) in 10 mL THF was added dropwise and stirred for 15 min at −70° C. Subsequently, 10 mL saturated NH$_4$Cl solution was added and the temperature allowed to reach RT. The layers were separated and the aqueous phase extracted with EtOAc (2×50 mL). The combined organic phases were washed with the crude product hydroxy-sulfone (21) as a mixture of diastereomers with complex NMR data. MS m/z 797 (M$^+$).

Sodium (1.5 g) was dissolved in 130 g Hg; 40 mL THF was added and the mixture cooled to −20° C. After the addition of 4 mL MeOH and 30 g KH$_2$PO$_4$, the hydroxy-sulfone mixture in 15 mL THF was added. The reaction continued for 6 hr (monitored by TLC (silica, CH$_2$Cl$_2$)) at −10° C. to −5° C. before water was added. The liquid phase was decanted, the residual Hg washed with water (exothermic) and EtOAc, and the layers were separated. The organic layers were washed with brine, dried (Na$_2$SO$_4$), and evaporated. Column chromatography (silica, CH$_2$Cl$_2$) afforded 440 mg (46%) of (22) as a white crystalline solid. NMR(CDCl$_3$): δ: 0 (s, 12H); 0.5 (s, 3H); 0.85 (s, 9H); 0.9 (s, 9H); 0.95 (d, 3H); 1.05 (d, 3H); 1.2–2 (m, 18H); 2.25 (d, 1H); 2.5 (dd, 1H); 2.7 (m, 1H); 2.85 (d, 1H); 4.2 (m, 1H); 4.5 (m, 1H); 4.65 (m, 2H); 4.9 (s, 1H); 4.95 (s, 1H); 5.25 (m, 2H); 5.8 (d, 1H); 6.4 (d, 1H). MS m/z 639(M$^+$).

A mixture of 140 mg of (22) in 35 mL toluene, with 5 drops of NEt$_3$ and 5 mg 9-acetylanthracene was irradiated for 4 hr under a constant stream of argon. This afforded 140 mg of the cis compound (23). NMR(CDCl$_3$): δ: 0 (s, 12H); 0.5 (s, 3H); 0.85 (s, 9H); 0.9 (s, 9H); 0.95 (d, 3H); 1.05 (d, 3H); 1.2–2 (m, 18H); 2.2 (m, 1H); 2.45 (dd, 1H); 2.8 (m, 2H); 4.2 (m, 1H); 4.35 (m, 1H); 4.7 (m, 2H); 4.85 (m, 1H); 5.15 (m, 1H); 5.25 (21H); 6 (d, 1H); 6.25 (d, 1H).

A mixture of 280 mg TBAF and 140 mg of (23) in 20 mL THF was stirred at 45° C. for 4 hr (monitored by TLC (silica, $CH_2Cl_2$)). The mixture was poured into 50 mL saturated $NaHCO_3$ solution and extracted with EtOAC. The organic layer was washed with water, brine and dried ($Na_2SO_4$). Evaporation of the solvents and chromatography (silica (EtOAc-hexane 2:1)) afforded 70 mg product as a white solid. The compound contained approximately 10% of the trans compound. Recrystallization from methylformate gave 15 mg (17%) of pure 1α-hydroxy-25-ene-vitamin $D_2$ (1). mp 134.6–138.4° C.; NMR($CDCl_3$): δ:0.5 (s, 3H); 0.95 (d, 3H); 1.05 (d, 3H); 1.05 (d, 3H); 1.2–2 (m, 185H); 2.25 (m, 1H); 2.55 (d, 1H); 2.65 (m, 1H); 2.8 (d, 1H); 4.2 (m, 1H); 4.4 (m, 1H); 4.65 (m, 2H); 4.95 (s, 1H); 5.2 (m, 2H); 5.3 (s, 1H); 6.0 (d, 1H); 6.35 (d, 1H); MS m/z 393($M^+$–18) 413 ($M^+$).

To a solution of 320 mg of (22) in THF was added 400 mg TBAF. The mixture was stirred at RT overnight, 3 hr at 55° C. and poured into 75 mL saturated $NaHCO_3$ solution. The mixture was extracted with EtOAc (2×50 mL) and the organic layers washed with brine, dried and the solvents evaporated. Column chromatography (silica (EtOAc-hexane 2:1)) gave a white solid which was dissolved in 40 mL toluene, and after the addition of 6 drops $NEt_3$ and 5 mg 9-acetylanthracene irradiated for 1.5 hr. Evaporation of the solvents followed by chromatography (silica (EtOAc-hexane 2:1)) gave 65 mg (31%) of 1α-hydroxy-25-ene-vitamin $D_2$ (1), with a purity of 96.7% (HPLC). UV: $\lambda_{max}$ 265 nm.

EXAMPLE 2

Synthesis of 24-hydroxy-25-ene-vitamin $D_2$

The synthesis of 24-hydroxy-25-ene-vitamin $D_2$ follows the same steps as given in Example 1 above except that hydroxylation steps at C-1 are eliminated and no protecting group is added to the carbon-i position. The product 25-ene-vitamin $D_2$ is then incubated with human hepatoma cells to yield the 24-hydroxylated product which is extracted and purified by known methods.

In summary, the present invention provides a method for preparing a novel class of vitamin D compounds in which the C-25 or equivalent position has a double bond. In addition, the side chain is optionally extended by one or two methylene or methyne groups. The compounds prepared by the method of the present invention are of value as prodrugs for active 1α, 24-dihydroxylated vitamin D compounds.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

What is claimed is:

1. A method of making a hydroxy-25-ene-vitamin D compound comprising the step of reacting a 2,3-dimethyl-3-butene phenyl sulfone with a hydroxyl-protected C-22 aldehyde of a vitamin D, the hydroxyl-protected C-22 aldehyde of vitamin D being hydroxyl-protected at C-3 or at C-3 and C-1.

2. A method of making a hydroxy-25-ene-vitamin $D_2$ compound comprising the step of reacting a 2,3-dimethyl-3-butene phenyl sulfone with a hydroxyl-protected C-22 aldehyde of a vitamin $D_2$, the hydroxyl-protected C-22 aldehyde of vitamin $D_2$ being hydroxyl-protected at C-3 or at C-3 and C-1.

3. The method of claim 2 wherein the C-22 aldehyde-phenyl sulfone reaction yields a hydroxyl-protected-25ene-vitamin D; and further comprising reducing, isomerizing, and deprotecting the hydroxyl-protected-25-ene-vitamin D to yield a hydroxy-25-ene-vitamin $D_2$.

4. The method of claim 1 wherein the vitamin D is a previtamin D.

5. The method of claim 2 wherein the C-22 aldehyde-phenyl sulfone reaction yields a hydroxyl-protected-25-ene-vitamin $D_2$; and further comprises reducing, isomerizing, deprotecting and irradiating the hydroxyl-protected-25-ene-vitamin D2 to yield a hydroxy-25-ene-vitamin $D_2$.

6. The method of claim 1 wherein the vitamin $D_2$ is a previtamin $D_2$.

7. The method of claim 1 wherein the vitamin $D_2$ is ergosterol.

* * * * *

UNITED STATES PATENT AND TRADEMARK OFFICE
CERTIFICATE OF CORRECTION

PATENT NO. : 6,441,207 B1
DATED : August 27, 2002
INVENTOR(S) : Hans Wynberg, Ton Vries and Kees Pouwer It is certified that error appears in the above-identified patent and that said Letters Patent is hereby corrected as shown below:

Column 2,
Line 39, "1,α25-" should red -- 1α,25 --.

Column 5,
Line 10, "10α,24-dihydroxylated" should read -- 1α,24-dihydroxylated --.
Line 57, "IV)," should read -- (IV), --.

Column 11,
Line 22, "6 units" should read -- δ units --.

Column 14,
Line 26, "ws" should read -- was --.

Column 15,
Line 41, "carbon-i" should read -- carbon-1 --.

Column 16,
Line 29, "hydroxyl-protected-25ene-" should read -- hydroxyl-protected-25-ene --.

Signed and Sealed this

Thirteenth Day of July, 2004

JON W. DUDAS
*Acting Director of the United States Patent and Trademark Office*